United States Patent
Mansour et al.

(10) Patent No.: US 10,414,957 B2
(45) Date of Patent: Sep. 17, 2019

(54) LOW APPLICATION TEMPERATURE HOT MELT ADHESIVE COMPOSITION

(71) Applicant: H.B. Fuller Company, St. Paul, MN (US)

(72) Inventors: Ameara S. Mansour, Woodbury, MN (US); Kevin P. Davis, Woodbury, MN (US); David B. Malcolm, Maplewood, MN (US); Mark S. Kroll, Arden Hills, MN (US); Steven R. Vaughan, Lake Elmo, MN (US); Timothy W. Roska, Forest Lake, MN (US); Evan Yuan, Guangzhou (CN)

(73) Assignee: H.B. Fuller Company, St. Paul, MN (US)

( * ) Notice: Subject to any disclaimer, the term of this patent is extended or adjusted under 35 U.S.C. 154(b) by 439 days.

(21) Appl. No.: 15/071,959

(22) Filed: Mar. 16, 2016

(65) Prior Publication Data

US 2016/0272856 A1  Sep. 22, 2016

Related U.S. Application Data

(60) Provisional application No. 62/133,784, filed on Mar. 16, 2015.

(51) Int. Cl.

| | | |
|---|---|---|
| *A61F 13/15* | (2006.01) | |
| *C09J 153/02* | (2006.01) | |
| *B32B 7/12* | (2006.01) | |
| *A61L 15/24* | (2006.01) | |
| *A61L 15/58* | (2006.01) | |
| *B32B 27/06* | (2006.01) | |
| *B32B 27/08* | (2006.01) | |
| *B32B 27/10* | (2006.01) | |
| *B32B 27/12* | (2006.01) | |
| *C09J 7/38* | (2018.01) | |

(52) U.S. Cl.
CPC ............ *C09J 153/02* (2013.01); *A61L 15/24* (2013.01); *A61L 15/58* (2013.01); *B32B 7/12* (2013.01); *B32B 27/06* (2013.01); *B32B 27/08* (2013.01); *B32B 27/10* (2013.01); *B32B 27/12* (2013.01); *C09J 7/387* (2018.01); *B32B 2270/00* (2013.01); *B32B 2274/00* (2013.01); *B32B 2405/00* (2013.01); *B32B 2555/02* (2013.01); *C09J 2201/606* (2013.01); *C09J 2201/61* (2013.01); *C09J 2201/622* (2013.01); *C09J 2205/114* (2013.01); *C09J 2425/00* (2013.01); *C09J 2453/00* (2013.01)

(58) Field of Classification Search
CPC .. C09J 153/02; C09J 7/0221; C09J 2201/606; C09J 2201/61; C09J 2201/622; C09J 2205/114; C09J 2453/00; A61L 15/58; B32B 7/12; B32B 27/06; B32B 27/08; B32B 27/10; B32B 27/12; B32B 2270/00; B32B 2274/00; B32B 2405/00; B32B 2555/02

See application file for complete search history.

(56) References Cited

U.S. PATENT DOCUMENTS

| | | | |
|---|---|---|---|
| 3,231,635 | A | 1/1966 | Geoffrey et al. |
| 3,239,478 | A | 3/1966 | Harlan, Jr. |
| 5,405,903 | A | 4/1995 | Westrenen et al. |
| 5,736,612 | A | 4/1998 | Van Dongen et al. |
| 6,162,859 | A | 12/2000 | Lu |
| 6,531,544 | B1 * | 3/2003 | Vaughan ............... A61L 24/043 525/89 |
| 6,582,829 | B1 | 6/2003 | Quinn et al. |
| 6,818,093 | B1 | 11/2004 | Tall et al. |
| 7,288,590 | B2 | 10/2007 | Lechat et al. |
| 7,309,522 | B2 | 12/2007 | Webb et al. |
| 7,439,301 | B2 | 10/2008 | Handlin, Jr. |
| 7,795,336 | B2 | 9/2010 | Paul et al. |
| 7,799,863 | B2 | 9/2010 | He et al. |
| 8,129,464 | B2 | 3/2012 | Abba et al. |
| 8,163,824 | B2 | 4/2012 | Okazaki et al. |
| 8,324,309 | B2 | 12/2012 | Dubois |
| 2005/0182183 | A1 | 8/2005 | He et al. |
| 2007/0117934 | A1 | 5/2007 | He et al. |
| 2013/0202787 | A1 | 8/2013 | Hu et al. |
| 2013/0225020 | A1 | 8/2013 | Flood et al. |
| 2013/0225752 | A1 | 8/2013 | Tse et al. |
| 2014/0364532 | A1 | 12/2014 | Dubois et al. |

FOREIGN PATENT DOCUMENTS

| | | |
|---|---|---|
| EP | 0451919 | 2/1995 |
| EP | 1761602 | 6/2012 |
| WO | WO 96/11236 | 4/1996 |

OTHER PUBLICATIONS

Kraton Innovations, "MD1648:A New Addition to the Kraton™ ERS Polymer Family", Market Launch Package, May 2014, pp. 1-20.

"Section III: Physical Properties of Monomers and Solvents," Polymer Handbook, By E.H. Immergut et al., 4th Ed., Wiley, 2005, pp. 34-36.(Year:2005).

(Continued)

*Primary Examiner* — Jacqueline F Stephens
(74) *Attorney, Agent, or Firm* — Kirsten Stone; Kristi Halloran

(57) ABSTRACT

This invention claims low application temperature hot melt adhesive compositions including at least about 15% by weight of a first styrene block copolymer with a melt flow rate of at least about 15 g/10 minutes (190° C., 2.16 kgs) and a diblock content of no greater than about 10% by weight.

20 Claims, No Drawings

(56) References Cited

OTHER PUBLICATIONS

"Temperature and Pressure Dependence of Viscosity." polymer Testing, by Wolfgang Grellmann and Sabine Seidler, Hanser Publishers, 2007, pp. 46-46.
TSRC/Dexco Polymers, "Low Melt Viscosity Hot Melt Adhesives Based on Radial Styrenic Block Copolymers" (presentation slides), World Adhesives and Sealants Conference. Sep. 2012.

* cited by examiner

LOW APPLICATION TEMPERATURE HOT MELT ADHESIVE COMPOSITION

This application claims the benefit of U.S. Provisional Application No. 62/133,784, filed Mar. 16, 2015, which is incorporated herein.

BACKGROUND

In the area of industrial adhesives, hot melt adhesives are commonly used to bond together a wide variety of articles including labels to containers and disposable absorbent articles comprising non-woven substrates e.g. adult incontinence products, disposable diapers, sanitary napkins, bed pads, puppy pads, medical dressings, etc.

Hot melt adhesive compositions often include a polymer and a tackifying agent, and in some cases wax or oil. Styrene block copolymers have been used as a polymer in such compositions.

Melt flow rate (MFR) is inversely related to the viscosity of a polymer. A higher MFR means that a polymer has a lower viscosity. Commercially available styrene block copolymers (SBC) work well in adhesives, but are not commonly commercially available with a high melt flow rate (i.e. >than 15 g/10 min (190° C., 2.16 kgs)). The grades that are available, often achieve the high melt flow rate with a high di-block content which can lower the mechanical properties of the polymer. This makes it difficult to formulate a low application temperature hot melt adhesive with good mechanical properties.

It would be desirable to be able to formulate a low application temperature hot melt adhesive based on SBC, with good mechanical properties. It would further be desirable to be able to formulate a hot melt adhesive with a higher amount of SBC, while maintaining a low viscosity.

SUMMARY

In one aspect, the invention includes a hot melt adhesive composition including: at least about 15% by weight of a first styrene block copolymer having an unsaturated mid-block, with a melt flow rate of at least about 15 g/10 minutes (190° C., 2.16 kgs) and a diblock content of no greater than about 10% by weight,
wherein the hot melt adhesive composition has a viscosity of no greater than about 15,000 cps at 121° C. In another embodiment, the hot melt adhesive composition has a viscosity of no greater than about 7,500 cps at 121° C. In still another embodiment, the hot melt adhesive composition has a viscosity of no greater than about 5,000 cps at 121° C.

In one embodiment, the first styrene block copolymer has a styrene content of from about 25% by weight to about 35% by weight. In another embodiment, the first styrene block copolymer has a diblock content of no greater than about 5% by weight. In a different embodiment, the first styrene block copolymer has a melt flow rate of from about 15 g/10 minutes (190° C., 2.16 kgs) to about 200 g/10 minutes (190° C., 2.16 kgs).

In one embodiment, the hot melt adhesive further includes a tackifying agent. In a different embodiment, it further comprising a plasticizer.

In another embodiment, the first styrene block copolymer, the tackifying agent and the plasticizer comprise at least about 80% by weight of the adhesive. In a different embodiment, the hot melt adhesive is a pressure sensitive adhesive.

In one embodiment, the first styrene block copolymer has a configuration selected from tri-block, multi-arm and radial. In another embodiment, the first styrene block copolymer has a tri-block configuration.

In a different embodiment, the hot melt adhesive composition has a Peel Force to Cotton of at least about 50 grams force (coat weight=25 gsm) when the adhesive is applied at 121° C. In one embodiment, the Spiral Spray T-Peel is at least about 50 grams force (coat weight=6.2 gsm) when the adhesive is applied at 121° C.

In another embodiment, the invention includes a disposable absorbent article comprising the hot melt adhesive. In one embodiment, the disposable absorbent article is selected from the group consisting of diaper, adult incontinence article, and sanitary hygiene article.

In one embodiment, the invention includes an adhesive tape or label comprising the hot melt adhesive.

In one aspect, the invention includes a hot melt adhesive composition including: at least about 25% by weight of a first styrene block copolymer with a melt flow rate of at least about 15 g/10 minutes (190° C., 2.16 kgs), a diblock content of no greater than about 10% by weight, and a styrene content of from about 25% by weight to about 35% by weight, a tackifying agent, and a plasticizer. In another embodiment, the first styrene block copolymer, the tackifying agent and the plasticizer include at least about 90% by weight of the adhesive.

In one embodiment, the plasticizer is present at no greater than about 20% by weight. In another embodiment, the invention includes a disposable absorbent article comprising: a topsheet; a backsheet; an absorbent core disposed between the topsheet and the backsheet; a garment-facing surface; and the pressure-sensitive adhesive composition disposed on the garment-facing surface of the absorbent article.

In a different aspect, the invention includes a disposable absorbent article comprising: a first substrate and a second substrate; and a hot melt adhesive composition applied to at least one of the first or second substrates, said hot melt adhesive composition comprising: at least about 15% by weight of a first styrene block copolymer with a melt flow rate of at least about 15 g/10 minutes (190° C., 2.16 kgs) and a diblock content of no greater than about 3% by weight, a tackfying agent, and a plasticizer; wherein the hot melt adhesive composition has a viscosity of no greater than about 7,500 cps at 121° C.

In one embodiment, the hot melt adhesive composition is used in the disposable article for an application selected from the group consisting of construction and positioning.

The hot melt adhesive compositions of this invention have low viscosities at 121° C. while having comparable mechanical properties (e.g. peel and creep) to higher viscosity hot melt adhesives. Other features and advantages will be apparent from the following descriptions of the preferred embodiments and from the claims.

DETAILED DESCRIPTION

The inventors have discovered hot melt adhesive compositions that can be applied at temperatures at or below 149° C., or even at or below 121° C. and still maintain good mechanical and adhesive properties. These properties make the adhesive composition useful for a variety of applications including labeling and the bonding of disposable absorbent articles.

Hot Melt Adhesive Composition

The adhesive composition is a hot melt adhesive. The hot melt adhesive can be a pressure sensitive adhesive.

In one embodiment, the first styrene block copolymer, tackifying agent and oil can make up at least about 80% by weight of the composition, or even at least about 90% by weight of the composition.

In one embodiment, the hot melt adhesive composition has Peel Force to Cotton of at least about 50 grams force (coat weight=25 gsm), at least about 100 grams force or even at least about 150 grams force when the adhesive is applied at 121° C.

In another embodiment, the hot melt adhesive composition has a Spiral Spray T-peel of at least about 50 grams force (coat weight=6.2 gsm), at least about 75 grams force or even at least about 100 grams force when the adhesive is applied at 121° C.

The hot melt adhesive composition has a low viscosity at application temperature. In one embodiment, the viscosity is no greater than no greater than about 10,000 cps, no greater than about 5,000 cps, from about 300 cps to 10,000 cps at 149° C., or even from about 500 cps to 5,000 cps at 149° C. In another embodiment, the viscosity is no greater than about 15,000 cps, no greater than about 10,000 cps, no greater than about 7,500 cps, from about 500 cps to about 15,000 cps, or even from about 1,000 cps to about 7,500 cps at 121° C.

Styrene Block Copolymer

First Styrene Block Copolymer

The hot melt adhesive composition includes a first styrene block copolymer with a melt flow rate of at least about 15 g/10 minutes (190° C., 2.16 kgs), at least about 20 g/10 minutes (190° C., 2.16 kgs), at least about 30 g/10 minutes (190° C., 2.16 kgs), at least about 50 g/10 minutes (190° C., 2.16 kgs) or even from about 15 to about 200 g/10 minutes (190° C., 2.16 kgs). The first styrene block copolymer has a diblock content of no greater than about 10% by weight, no greater than about 5% by weight, no greater than about 3% by weight, or even no greater than about 1% by weight.

The composition can include more than one first styrene block copolymer with a melt flow rate of at least about 15 g/10 minutes (190° C., 2.16 kgs) and a diblock content of no greater than about 10% by weight.

The first styrene block copolymer includes an aromatic vinyl polymer block and a conjugated diene polymer block, a hydrogenated conjugated diene polymer block, or a combination thereof. The blocks can be arranged in a variety of configurations including, e.g., linear, branched, radial, star and combinations thereof. The aromatic vinyl polymer block can be derived from a variety of aromatic vinyl compounds including, e.g., styrene, alpha-methylstyrene, beta-methylstyrene, o-, m-, p-methylstyrene, t-butylstyrene, 2,4,6-trimethylstyrene, monofluorostyrene, difluorostyrene, monochlorostyrene, dichlorostyrene, methoxystyrene, 1,3-vinylnaphthalene, vinylanthracene, indene, acenaphthylene, and combinations thereof. The diene polymer block can be derived from a variety of diene-containing compounds including, e.g., isoprene, butadiene, hexadiene, 2,3-dimethyl-1,3-butadiene, 1,3-pentadiene, and hydrogenated versions thereof, and combinations thereof.

Useful first styrene block copolymers include, e.g., triblock, multi-arm and radial copolymers including, e.g., styrene-butadiene-styrene (SBS), styrene-isoprene-styrene (SIS), styrene-butadiene-isobutylene-styrene (SBBS), styrene-isoprene-butadiene-styrene (SIBS), styrene-ethylene/butene-styrene (SEBS), styrene-ethylene/propylene-styrene (SEPS), styrene-ethylene-ethylene/propylene-styrene (SEEPS), and combinations thereof.

The first styrene block copolymer can have a styrene content of at least about 18% by weight, at least about 25% by weight, at least about 30% by weight, no greater than about 35% by weight, no greater than about 47% by weight, from about 30% to about 47% by weight, from about 30% to about 37% by weight, from 25% by weight to 35% by weight, or even from about 30% to about 35% by weight.

The first styrene block copolymer can have an unsaturated mid-block, alternately the mid-block can be saturated i.e. hydrogenated. The first styrene block copolymer can be selected from the group consisting of SIS, SBS, SIBS, and SBBS. The first styrene block copolymer can be a blend of one or more styrene block copolymers.

The first styrene block copolymer can be the only polymer present in the adhesive. The first styrene block copolymer can be present in the adhesive at, at least about 15% by weight, at least about 20% by weight, at least about 25% by weight, from about 15% by weight to about 60% by weight, or even from about 18% by weight to about 40% by weight.

Useful first styrene block copolymers include for example KRATON MD 1648 commercially available from Kraton Polymers US LLC (Houston, Tex.).

The composition can include other styrene block copolymers in addition to the first styrene block copolymer. Useful additional styrene block copolymers include VECTOR 4411 and VECTOR 6241 available from TSRC Corporation (Houston, Tex.) and SOLPRENE 411 (a high molecular weight radial SBS block copolymer) available from Dynasol (Houston, Tex.).

Plasticizer

The adhesive composition can optionally include a plasticizer. Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives and combinations thereof.

Useful commercially available plasticizers include CALSOL 550 and CALSOL 5550 oil from Calumet Specialty Products Partners, LP (Indianapolis, Ind.), KAYDOL OIL from Sonneborn (Tarrytown N.Y.), KRYSTOL 550 mineral oil from Petrochem Carless Limited (Surrey, England), PURETOL 35 mineral oil from Petro Canada Lubricants Inc. (Mississauga, Ontario) and TPC 5230, and polyisobutylene available from TPC Group (Houston, Tex.).

The plasticizer if present in the adhesive composition can be present at from about 5% by weight to about 40% by weight, or even from about 10% by weight to about 30% by weight.

Tackifying Agent

The hot melt adhesive composition can include a tackifying agent. The tackifying agent can comprise one or more tackifying agents. The tackifying agent can be at least partially hydrogenated in order to improved stability. The tackifying agent can be fluid or solid at room temperature. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

Useful resins are commercially available under a variety of trade designations including, e.g., the ESCOREZ series of trade designations from Exxon Mobil Chemical Company (Houston, Tex.) including ESCOREZ 1310 LC, ESCOREZ 5400, ESCOREZ 5415, ESCOREZ 5600, ESCOREZ 5615, and ESCOREZ 5690, the EASTOTAC series of trade designations from Eastman Chemical (Kingsport, Tenn.) including EASTOTAC H-100R, EASTOTAC H-100L, and EASTOTAC H130W, the WINGTACK series of trade designations from Cray Valley HSC (Exton, Pa.) including WINGTACK 86, WINGTACK EXTRA, and WINGTACK 95, the PICCOTAC, PICCOTEX, KRISTALEX and PLASTOLYN series of trade designations from Eastman Chemical Company (Kingsport, Tenn.) including, e.g., PICCOTEX 120, PICCOTAC 8095, KRISTALEX 3100, PLASTOLYN 240 and PLASTOLYN 290, the SUKOREZ trade designations from Kolon Industries Inc., Korea including, e.g., SUKOREZ SU-90, SUKOREZ SU-100, and SUKOREZ SU-120, the SYLVARES and ZONATAC trade designations from Arizona Chemical (Jacksonville, Fla.) including e.g., SYLVARES TR 7115, SYLVARES SA 140 and ZONATAC NG 98.

In one embodiment, there are at least two resins comprising at least one aromatic hydrocarbon resin and at least one aliphatic hydrocarbon resin. Aromatic hydrocarbon resins may also be referred to as end block reinforcing resins. Aliphatic hydrocarbon resins may be referred to as midblock modifying/tackifying resins. The aromatic hydrocarbon resin (endblock reinforcing resin) may be employed to impart further cohesive strength. The aliphatic hydrocarbon resin (midblock modifying resin) is used for providing sufficient tack.

Examples of suitable aliphatic hydrocarbon resins include but are not limited to aliphatic and cycloaliphatic hydrocarbon resins, hydrogenated hydrocarbon resins, terpenes, modified terpenes and hydrogenated versions thereof; natural rosins, modified rosins, rosin esters, and hydrogenated versions thereof; and combinations thereof, including slightly aromatic resins having a content of aromatic monomers of up to 15 weight %. Preferably, the aliphatic hydrocarbon resin is hydrogenated.

Suitable examples of the aromatic hydrocarbon resin include but are not limited to aromatic hydrocarbon resins comprising monomers selected from the group consisting of styrene, alpha methyl styrene, vinyl toluene, indene, or any other aromatic monomer or end block associating monomer. Aromatic hydrocarbon resins can have greater than 50% by weight aromatic content, or even greater than 60% aromatic content.

The adhesive composition can include from about 5% by weight to about 60% by weight, from about 10% by weight to about 50% by weight, or even from about 10% by weight to about 40% by weight tackifying agent.

Wax

The adhesive composition can include a wax. Useful classes of wax include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxy modified waxes, animal waxes, vegetable waxes (e.g. soy wax) and combinations thereof. Useful waxes are solid at room temperature and preferably have a Ring and Ball softening point of from 50° C. to 170° C. Useful waxes are commercially available from a variety of suppliers including EPOLENE N and C series of trade designations from Westlake Chemical Corporation (Houston, Tex.) including e.g. EPOLENE N-21 and the LICOCENE series of trade designations from Clariant International Ltd. (Muttenz, Switzerland) including e.g. TP LICOCENE PP 6102.

The adhesive composition can include no greater than about 10% by weight, no greater than about 5% by weight, from about 1% by weight to about 10% by weight, from about 1% by weight to about 5% by weight wax, or even from about 1% by weight to about 3% by weight wax.

Additional Polymers

The adhesive composition optionally includes additional polymers (e.g. single-site catalyzed polyolefins, amorphous poly-alpha olefins, polyethylene homopolymers/copolymers and polypropylene homopolymers/copolymers). Useful additional polymers include VISTAMAXX 6102 (propylene/ethylene copolymer) available from ExxonMobil Chemical (Houston, Tex.) and REXTAC 2730 (an amorphous poly-alpha olefin) available from Rextac LLC (Odessa, Tex.).

Additional Components

The adhesive composition optionally includes additional components including, e.g., stabilizers, antioxidants, adhesion promoters, ultraviolet light stabilizers, corrosion inhibitors, colorants (e.g., pigments and dyes), fillers, surfactants, wetness indicators, superabsorbents and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J., and ETHYL 702 4,4'-methylene bis(2,6-di-tert-butylphenol). When present, the adhesive composition preferably includes from about 0.1% by weight to about 2% by weight antioxidant.

End Uses

The adhesive compositions of this invention can be used in many different applications and for a variety of end uses including pressure sensitive adhesives (e.g. removable and permanent types), bookbinding adhesives, adhesives to attach inserts to published materials (e.g. magazines), adhesives to assemble various items (e.g. filters), adhesives for packaging constructions (e.g. cases, cartons, trays, etc.), adhesives for tapes and labels, and adhesives for disposable articles.

Tapes and Labels

The adhesive composition can be used to make adhesive tapes or alternately to adhere labels to various items (e.g. containers, magazines, etc.). The label/tape can be selected from a variety of materials including paper, non-paper films (e.g. polypropylene (e.g. polypropylene (PP), oriented polypropylene (OP), and biaxially oriented polypropylene (BOPP)), polyethylene, etc.). The container can be metal (e.g. aluminum or steel) or plastic (polyethylene terephthalate (PET), high density polyethylene (HDPE) and polypropylene.

The label can be a spot label i.e. a label that does not extend completely around the container. Alternatively, the label can be a wrap around label i.e. a label that completely wraps around the entire container.

If the label is a wrap around label, it can be roll fed into the applicator. Alternatively, the labels are pre-cut and fed in from a stack. In a wrap around label application method, the label stock is fed into a label station. A pick-up adhesive and a lap glue are then applied to the label, often from the same glue pot. A pick-up adhesive adheres the leading edge of the label to a container. The lap glue then bonds the overlap where the wrap around label overlaps itself. The adhesive composition of this invention can be both the pick-up adhesive and the lap glue.

Disposable Absorbent Article

The adhesive composition can be applied to (i.e. such that it is in direct contact with) or incorporated in a variety of substrates including, e.g., films (e.g., polyolefin (e.g., polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers) and tape backings.

The adhesive composition is also useful in a variety of applications and constructions including, e.g., disposable absorbent articles including, e.g., disposable diapers, adult incontinence products, sanitary napkins, medical dressings (e.g., wound care products) bandages, surgical pads, nursing pads, pet training pads (e.g. puppy pads) and meat-packing products and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue) and elastics.

The ability to apply the adhesive composition at lower temperatures (e.g. 121° C.) makes the adhesive compositions particularly useful for bonding materials (e.g. nonwoven webs, back sheets, tissues, etc.) that are low in basis weight, thermally sensitive, or have a low gauge (i.e. thickness). On these sensitive substrates, standard application temperatures can result in strike through (adhesive soaking through substrate) or deformation (i.e. melting, burning, etc.) of the substrate.

In one embodiment, the low gauge materials are no greater than 15 microns in thickness, no greater than 12 microns in thickness, or even no greater than 10 microns in thickness. In one embodiment, the low basis weight materials have a basis weight of no greater than 12 grams per square meter (gsm), or even no greater than 10 gsm.

The adhesive composition is useful on substrates made from a variety of fibers including, e.g., natural cellulose fibers such as wood pulp, cotton, silk and wool; synthetic fibers such as nylon, rayon, polyesters, acrylics, polypropylenes, polyethylene, polyvinyl chloride, polyurethane, and glass; recycled fibers, and various combinations thereof.

Various application techniques can be used to apply the composition to a substrate including, e.g., slot coating, spraying including, e.g., spiral spraying and random spraying, screen printing, foaming, engraved roller, extrusion and meltblown application techniques.

Methods of Making a Disposable Absorbent Article

The adhesive composition is low in viscosity and has good mechanical properties. These properties make it useful for multiple applications in the construction of a disposable absorbent article.

The adhesive is useful for elastic attachment applications, which include bonding elastic material to either the leg and/or waist area. The elastic material can be bonded to polyethylene, polypropylene or nonwoven substrates to result in creep resistant gathers.

The adhesive can also be used for construction applications. In a typical construction application in the manufacture of a disposable absorbent article, a body fluid impermeable backsheet is bonded to a nonwoven substrate. The adhesive may also be used to bond at least one additional layer or material selected from the group consisting of absorbents, tissues, elastomeric materials, superabsorbent polymers, and combinations thereof. For example, the adhesive can further be used for back sheet lamination i.e. where the body fluid impermeable backsheet typically a polyolefin film (e.g. polyethylene, polypropylene, ethylene vinyl acetate, ethylene copolymer, etc.) is bonded to a second nonwoven to improve the feel of the disposable article.

The adhesive can be used to contain and/or provide strength to the absorbent core of a disposable absorbent article (i.e. as a core stabilization adhesive). The absorbent core can include many different materials including natural cellulose fibers (e.g. wood pulp, fibers, cotton, fluff, etc.) and superabsorbent polymers (e.g. polyacrylates). In some disposable absorbent articles, the absorbent core is substantially cellulose free. In a cellulose free core, the absorbent core consists of adhesive and superabsorbent polymer.

The adhesive can be used as a positioning adhesive. A positioning adhesive is a class of adhesive compositions that is often used to position feminine hygiene articles, such as sanitary napkins, nursing pads, etc. on undergarments, e.g., cotton undergarments. These articles are removed from the undergarment after use. When the article is removed from the undergarment, preferably no adhesive composition remains on the undergarment (i.e., the undergarment is free of adhesive transfer).

The invention will now be described by way of the following examples. All parts, ratios, percents and amounts stated in the Examples are by weight unless otherwise specified.

EXAMPLES

Test Procedures

Test procedures used in the examples and throughout the specification, unless stated otherwise, include the following.

Viscosity Test Method

Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipoise (cps).

Melt Flow Rate

Melt Flow Rate is determined according to ASTM D 1238 at the stated conditions.

Peel Force to Stainless Steel Sample Preparation Method

A laminate is prepared by coating a sample composition onto an untreated Mylar film in a one inch wide pattern at an add-on weight of 20 $g/m^2$ using a slot applicator and then contacting the adhesive strip with the treated side of a 2 mil (0.05 mm) thick Mylar release film to form a release treated Mylar/adhesive/untreated Mylar film laminate. Test samples having a length of 84 inches (in) (23.32 cm) in the machine direction and 1.5 in (3.81 cm) in the cross-machine direction are then cut from the laminate such that the adhesive pattern is centered in the cross-machine direction of the test sample.

The release layer is then removed and the adhesive is applied to a stainless steel panel having a length of 8 in (20.32 cm) and a width of 3 in (7.62 cm). In preparing the composite test sample, the adhesive is not pressed down onto the stainless steel.

Peel Force to Stainless Steel Test Method

Three samples are prepared according to the Peel Force to Stainless Steel Sample Preparation Method. Each test sample is placed on a 2 kg mechanical roll-down device and the roller is allowed to pass over the film side of the sample two times, once in the forward direction and once in the backward direction, at a rate of 305 mm/min. A timer is then activated and the sample is placed into the jaws of INSTRON-type peel tester. After one minute, the sample is peeled at a 180 degree angle according to PSTC 101 entitled, "Peel Adhesion of Pressure Sensitive Tape," and the peel force is recorded. The average peel force of the three samples is reported in Newtons (N).

Shear Adhesion Failure (SAFT) Test Sample Preparation

Adhesive laminates used for SAFT testing are prepared by coating a sample composition on a Mylar release film in a one inch wide pattern and at an add-on weight of 20 g/m$^2$ using a slot applicator. The adhesive is then transferred to an untreated Mylar film (i.e., a Mylar film without release properties) to form a Mylar film/adhesive/Mylar film laminate. Samples are then cut from the laminate to a length of one inch in the machine direction and three inches in the cross-machine direction such that the adhesive is present at one end of the sample. The Mylar release film is then removed from each of two samples to expose the one square inch area of the adhesive present on the end of each sample. The exposed adhesive of a first sample is then contacted with the exposed adhesive of a second sample to form a test sample that is five inches long and has a one inch overlap in the center. The adhesive overlap has an area of 2.54 cm$^2$ and a total add-on level of 40 g/m$^2$.

SAFT Test Method

Test samples are prepared according to the SAFT Test Sample Preparation Method. Each test sample is placed on a 2 kg mechanical roll-down device, and the roller is allowed to pass twice over the sample, once in the forward direction and once in the backward direction, at a rate of 305 mm/min. The shear adhesion failure (SAFT) of the test sample is determined by placing a test sample in a programmed oven, applying a shear force with a 500 g weight and ramping the temperature up from 25° C. to 175° C. at a rate of 25° C. per hour according to ASTM D-4498 entitled, "A Standard Test Method for the Heat-fail Temperature in Shear of Hot Melt Adhesives." The oven automatically records the temperature at which the test sample fails. The result reported is the average failure temperature of four test samples. The result is reported in degrees Celsius.

Static Shear Test

The Static Shear Test was performed according to ASTM D3654D Test Method for Holding Power of Pressure-Sensitive Tape Loop Tack The Loop Tack was performed according ASTM D 6195-97.

Test Sample Preparation Method for Peel Force to Cotton

A laminate is prepared by coating a sample composition onto a Mylar release film in a one inch wide pattern at the specified add on weight per square meter (g/m$^2$) (+/−3 g/m$^2$) and the specified application temperature, using a slot applicator and then contacting the adhesive strip with the treated side of a 1 mil (0.025 mm) thick polyethylene film to form a Mylar film/adhesive/polyethylene film laminate. Test samples having a length of 4 inches (in) (10.16 cm) in the machine direction and 1.5 in (3.81 cm) in the cross-machine direction are then cut from the laminate such that the adhesive pattern is centered in the cross-machine direction of the test sample.

Strips of cotton fabric having a length of 4 in (10.16 cm) in the machine direction and a width of 1.5 in (3.81 cm) in the cross-machine are cut from 124 g/m$^2$ bleached t-shirt cotton fabric (Testfabrics, Inc., West Pittston, Pa.). Before cutting the cotton fabric, the grid work of the stitching of the fabric is examined. When the cotton fabric is stretched, the sample will exhibit greater elongation in one direction than in another direction. The cotton fabric is cut lengthwise in the direction that has less elongation. All cotton fabric strips are cut as straight as possible along the stitching grid work. If the cotton fabric strips are cut askew, an inconsistent elongation of the cotton fabric test sample will result.

The release film is removed from the adhesive and the adhesive side of each test sample is gently placed on the surface of a cotton strip such that the cotton curls up (in the lengthwise direction) toward the adhesive bond to form the composite test sample. In preparing the composite test sample, the adhesive is not pressed down onto the cotton fabric.

Peel Force to Cotton Test Method

Seven samples are prepared according to the Peel Force and Adhesive Transfer Test Sample Preparation Method. The test sample is placed on a 2 kg mechanical roll-down device and the roller is allowed to pass over the film side of the sample two times, once in the forward direction and once in the backward direction, at a rate of 305 mm/min. A timer is then activated and the sample is placed into the jaws of INSTRON-type peel tester. The polyethylene film is placed into the moving jaw, and the cotton fabric is attached to the stationary jaw. Within one minute after the sample has been removed from the roll-down device, the sample is tested according to ASTM D1876-01 entitled, "Test Method for Determining Peel Resistance of Adhesive (T-Peel Test Method)," with the exception that the test is run at a rate of 305 mm/min, instead of 250 mm/min, over a period of ten seconds, and seven replicates are run instead of the ten specified in ASTM D1876. The average peel force over ten seconds of peeling is recorded, and the results are reported in grams.

The initial peel force is measured 24 hours after the test sample is prepared. The two week peel force is measured after the test sample has been subjected to accelerated aging at 50° C. for two weeks. The four week peel force is measured after the test sample has been subjected to accelerated aging at 50° C. for four weeks. After the test was complete the cotton portion of the peeled sample was evaluated for adhesive transfer. If there was no visible adhesive transfer to the cotton, the sample was give a "No" rating.

T-Peel Test Sample Preparation

A multi-bead applicator and laminator are set to the application temperature indicated in Table 3, a nip pressure of 15 psi, an application weight shown in Table 3, and minimal rewind and unwind tensions so as not to stretch film. The spiral spray pattern is 1.27 cm (0.5 inches) wide with 6-8 spirals per inch. The fine line pattern is applied at 1.4 mg/in. A 1 mil thick white embossed polyethylene film that includes a blend of linear low density polyethylene and low density polyethylene (e.g., DH-284 PE MICROFLEX Embossed Non-Breathable film having an emboss gauge of 1.8 mils (ASTM D374), 70 gram F50 impact strength (ASTM D1709), 670% elongation at break in the machine direction (ASTM D882), 920% elongation at break in the cross direction (ASTM D882), 590 grams tensile at 10% elongation in the machine direction (ASTM D882), 550 grams tensile at 10% elongation in the cross direction (ASTM D882), 2500 ultimate tensile in the machine direction (ASTM D882), and 1700 grams ultimate tensile in the cross direction (ASTM D882) available from Clopay Plastic Products Company, Inc., (Cincinnati, Ohio) or equivalent thereof), which has been corona treated on one side thereof to surface energy of 38 dynes per square centimeter (dynes/$cm^2$) (as measured using dynes pens), is passed through the applicator. The specified coat weight and pattern of adhesive is applied to the corona treated side of the polymer film and then the film and adhesive are nipped to a 15 grams/square meter ($g/m^2$) basis weight spunbond polypropylene nonwoven web having a 7 mil Thwing-Albert thickness (e.g., UNIPRO 45 nonwoven web from Midwest Filtration Company) to form a laminate.

The speed at which the film passes through the applicator is from 400 feet per minute (ft/min) to 900 ft/min and the adhesive coat weight is 1.4 mg/in. A sufficient amount of laminate is prepared such that 60 inches of representative lamination can be collected for testing.

T-Peel Test Method

The T-Peel test is used to measure the bond strength of an adhesive coated between two flexible substrates. T-Peel is determined using ASTM D1876-01 entitled, "Test Method for Determining Peel Resistance of Adhesive (T-Peel Test Method)," with the exception that it is run at 12 inches per minute, instead of 10 in per minute, over a period of 10 seconds, and 7 replicates are run instead of the 10 specified in ASTM D1876. The samples are run on an INSTRON type test instrument. Unless otherwise specified, the test samples are prepared as described in the Sample Preparation. The average peel value over 10 seconds of peeling is recorded, and the results are reported in grams. The initial T-Peel value is the value measured 24 hours after the laminate is prepared.

Rheological Creep (% Strain at 20 Minutes)

Rheological Creep was run on a TA Instruments AR-G2 rheometer using parallel plate geometry with an 8 mm plate. The test was run isothermally at 38° C. with a gap of 300 rm.

Once equilibrated at 38° C., a pressure of 26,800 Pa was applied. The sample was held at this pressure for 20 minutes. The % strain at 20 minutes was then measured.

Polymer Descriptions

Polymer Example 1 is a <1 weight % diblock, SIS tri-block co-polymer containing 30% by weight styrene and having a MFR of 168 (190° C., 2.16 kgs).

Polymer Example 2 is a <1 weight % diblock, SIS tri-block co-polymer containing 30% by weight styrene and having a MFR of 34 (190° C., 2.16 kgs).

Polymer Example 3 is a <1 weight % diblock, SIS tri-block copolymer containing 44% by weight styrene and having a MFR of 155 (190° C., 2.16 kgs).

Polymer Example 4 is a <1 weight % diblock, SBS tri-block copolymer containing 43% by weight styrene and having a MFR of 79 (190° C., 2.16 kgs).

Polymer Example 5 is a <1 weight % diblock, SBS tri-block copolymer containing 43% by weight styrene and having a MFR of 23 (190° C., 2.16 kgs).

Vector 4211A is a <1% by weight diblock, SIS tri-block co-polymer containing 30% by weight styrene and having a MFR of 2.5 (190° C., 2.16 kgs).

Vector 6241A is a <1% by weight diblock, SBS tri-block co-polymer containing 43% by weight styrene and having a MFR of 5.0 (190° C., 2.16 kgs).

Adhesive Descriptions

NW1043 ZP is a regular application temperature (149° C.) positioning adhesive available from HB Fuller Company.

NW1140 ZP is a regular application temperature (149° C.) construction adhesive available from HB Fuller Company.

TABLE 1

General use pressure sensitive adhesive for tape/label

|  | Control 1 | Example 1 |
|---|---|---|
| VECTOR 4211A | 22 |  |
| Polymer Example 1 (SIS, MFR = 168, 30% styrene) |  | 22 |
| ESCOREZ 5400 | 49 | 49 |
| ESCOREZ 2203 |  |  |
| CALSOL 550 | 27.5 | 27.5 |
| IRGANOX 1076 | 0.2 | 0.2 |
| Viscosity @ 107° C. (225° F.) - cps | 43150 | 5200 |
| Viscosity @ 121° C. (250° F.) - cps | 9550 | 2410 |
| Viscosity @ 135° C. (275° F.) - cps | 4100 | 1300 |
| Viscosity @ 149° C. (300° F.) - cps | 2140 | 775 |
| Mettler Softening Point - ° C. (° F.) | 90.1 (194.2) | 66.1 (150.9) |
| Peel to Stainless Steel (Newtons) | 3.2 | 2.9 |
| Loop Tack (oz) | 84 | 81 |
| SAFT - ° C. (° F.) | 68.3 (155) | 58.3 (128) |
| Static Shear @ 40° C. (1" × 1") - 1 kg weight (hours) | >24 | 7 |

TABLE 2

Positioning adhesives for disposable articles

|  | Compar. 1 (NW1043 ZP) | Example 2 | Example 3 | Control 2 | Example 4 |
|---|---|---|---|---|---|
| Polymer Example 1 (SIS, MFR = 168, 30% styrene) |  | 19 | 25 |  |  |
| Polymer Example 3 (SIS, MFR = 155, 44% styrene) |  |  |  |  | 23 |
| VECTOR 4411 A |  |  |  | 23 |  |
| ESCOREZ 5600 |  | 30 | 30 |  |  |
| ESCOREZ 5400 |  |  |  | 57 | 57 |
| ESCOREZ 2203 |  | 25.5 | 25.5 |  |  |
| CALSOL 550 |  | 25 | 19 |  |  |
| PURETOL 35 |  |  |  | 19.5 | 19.5 |
| IRGANOX 1076 |  | 0.5 | 0.5 | 0.5 | 0.5 |
| Visc @ 93° C. (200° F.) - cps | NT | 23200 |  |  |  |

TABLE 2-continued

Positioning adhesives for disposable articles

|  | Compar. 1 (NW1043 ZP) | Example 2 | Example 3 | Control 2 | Example 4 |
|---|---|---|---|---|---|
| Visc @ 107° C. (225° F.) - cps | NT | 6625 | 16100 |  | 3490 |
| Visc @ 121° C. (250° F.) - cps | 30000 | 2400 | 6372 |  |  |
| Visc @ 135° C. (275° F.) - cps | 6500 | 1287 | 3050 | 10220 | 1697 |
| Visc @ 149° C. (300° F.) - cps | 2250 | 770 | 1672 | 3050 | 959 |
| Visc @ 163° C. (325° F.) - cps |  |  |  | 1405 | 525 |
| Peel Force to Cotton (avg - grams) |  |  |  |  |  |
| 25 gsm, applied @ 149° C. | 295 |  |  |  |  |
| 15 gsm, applied @ 149° C. | 170 |  |  |  |  |
| 25 gsm, applied @ 121° C. |  | 347 |  |  |  |
| 15 gsm, applied @ 121° C. |  | 212 |  |  |  |
| 25 gsm, applied @ 107° C. |  | 361 |  |  |  |
| Adhesive transfer to cotton? | No | No |  |  |  |

TABLE 3

Construction adhesives for disposable articles

|  | Compar. 2 (NW1140 ZP) | Example 5 | Example 6 | Control 3 | Example 7 | Example 8 |
|---|---|---|---|---|---|---|
| VECTOR 6241A (SBS, MFR = 5, 30% styrene) |  |  |  | 25 |  |  |
| Polymer Example 1 (SIS, MFR = 168, 30% styrene) |  | 18 |  |  |  |  |
| Polymer Example 3 (SIS, MFR = 34, 30% styrene) |  |  | 18 |  |  |  |
| Polymer Example 4 (SBS, MFR = 79, 43% styrene) |  |  |  |  | 25 |  |
| Polymer Example 5 (SBS, MFR- = 23, 43% styrene) |  |  |  |  |  | 25 |
| ESCOREZ 5400 |  | 61.5 | 61.5 |  |  |  |
| ZONATAC NG 98 |  |  |  | 54.8 | 54.5 | 54.5 |
| CALSOL 550 |  | 20 | 20 | 20 | 20 | 20 |
| IRGANOX 1076 |  | 0.5 | 0.5 | 0.5 | 0.5 | 0.5 |
| Visc@ 93° C. (200° F.) - cps | NT | 30600 | 42800 |  | 31700 | 45000 |
| Visc@ 107° C. (225° F.) - cps | NT | 9475 | 10300 | 41500 | 10650 | 14700 |
| Visc@ 121° C. (250° F.) - cps | NT | 3485 | 4100 | 16400 | 4450 | 6000 |
| Visc@ 135° C. (275° F.) - cps | 11500 | 1580 | 1950 | 7700 | 2220 | 2840 |
| Visc@ 149° C. (300° F.) - cps | 2900 | 865 |  | 4150 | 1180 | 1540 |
| Visc@ 163° C. (325° F.) - cps |  |  |  | 2250 |  |  |
| Avg Spiral Spray T-Peel (g) |  |  |  |  |  |  |
| 6.2 gsm (spiral spray) @ 149° C. | 108 |  |  | 128 |  |  |
| 4.0 gsm (spiral spray) @ 149° C. | 59 |  |  | 76 |  |  |
| 1.4 mg/in (fine line) @ 149° C. | 57 |  |  | 106 |  |  |
| 6.2 gsm (spiral spray) @ 121° C. |  | 103 | 113 |  | 123 | 130 |
| 4.0 gsm (spiral spray) @ 121° C. |  | 52 | 72 |  | 84 | 87 |
| 1.4 mg/in (fine line) @ 121° C. |  | 120 | 105 |  | 103 | 106 |

TABLE 4

Elastic attachment adhesives for disposable articles

|  | Control 4 | Example 9 |
|---|---|---|
| VECTOR 6241A (SBS, MFR = 5, 30% STYRENE) | 20 |  |
| Polymer Example 5 (SBS, MFR- = 23, 43% styrene) |  | 20 |
| ESCOREZ 5600 | 59.5 | 59.5 |
| PLASTOLYN 290 | 5 | 5 |
| CALSOL 550 | 15 | 15 |
| IRGANOX 1076 | 0.5 | 0.5 |
| Visc@ 93° C. (200° F.) - cps |  |  |
| Visc@ 107° C. (225° F.) - cps |  | 38700 |
| Visc@ 121° C. (250° F.) - cps | 22650 | 13700 |
| Visc@ 135° C. (275° F.) - cps | 9775 | 5850 |
| Visc@ 148° C. (300° F.) - cps | 4825 | 2870 |
| Visc@ 162° C. (325° F.) - cps | 2660 |  |
| Creep (% strain at 20 minutes) | 4 | 5 |

Other embodiments are within the claims.

What is claimed is:

1. A hot melt adhesive composition comprising:
a first styrene block copolymer having an unsaturated midblock, a melt flow rate of at least about 15 g/10 minutes (190° C., 2.16 kgs) and a diblock content of no greater than about 10% by weight,
the hot melt adhesive composition having a viscosity of no greater than about 15,000 cps at 121° C.

2. The hot melt adhesive composition of claim 1 wherein the hot melt adhesive composition has a viscosity of no greater than about 7,500 cps at 121° C.

3. The hot melt adhesive composition of claim 1 wherein the first styrene block copolymer is the only styrene block copolymer present in the hot melt adhesive.

4. The hot melt adhesive composition of claim 1 wherein the first styrene block copolymer has a diblock content of no greater than about 5% by weight.

5. The hot melt adhesive composition of claim 1 wherein the first styrene block copolymer has a melt flow rate of from about 15 g/10 minutes (190° C. 2.16 kgs) to about 200 g/10 minutes (190° C., 2.16 kgs).

6. The hot melt adhesive of claim 1 further comprising a tackifying agent.

7. The hot melt adhesive of claim 6 further comprising a plasticizer.

8. The hot melt adhesive of claim 7 wherein the first styrene block copolymer, the tackifying agent and the plasticizer comprise at least about 80% by weight of the adhesive.

9. The hot melt adhesive composition of claim 7 wherein the hot melt adhesive is a pressure sensitive adhesive.

10. An adhesive tape or label comprising the hot melt adhesive of claim 7.

11. The hot melt adhesive composition of claim 1 wherein the first styrene block copolymer has a tri-block configuration.

12. The hot melt adhesive composition of claim 1 wherein the Peel Force to Cotton is at least about 50 grams force (coat weight=25 gsm) when the adhesive is applied at 121° C.

13. The hot melt adhesive composition of claim 1 wherein the Spiral Spray T-Peel is at least about 50 grams force (coat weight=6.2 gsm) when the adhesive is applied at 121° C.

14. A disposable absorbent article comprising the hot melt adhesive of claim 1.

15. The disposable absorbent article of claim 14 selected from the group consisting of diaper, adult incontinence article, and sanitary hygiene article.

16. A hot melt adhesive composition comprising:
a.) at least about 15% by weight of a first styrene block copolymer with a melt flow rate of at least about 15 g/10 minutes (190° C., 2.16 kgs), a diblock content of no greater than about 10% by weight, and a styrene content of from about 25% by weight to about 35% by weight,
b.) a tackifying agent, and
c.) a plasticizer,
the hot melt adhesive composition having a viscosity of no greater than about 15,000 cps at 121° C.

17. The hot melt adhesive composition of claim 16 where the sum of a.), b.) and c.) is at least 90% of the composition.

18. A disposable absorbent article comprising:
a topsheet;
a backsheet;
an absorbent core disposed between the topsheet and the backsheet;
a garment-facing surface; and
the hot melt adhesive composition of claim 16 disposed on the garment-facing surface of the absorbent article.

19. A disposable absorbent article comprising:
a first substrate and a second substrate; and
a hot melt adhesive composition applied to at least one of the first or second substrates, said hot melt adhesive composition comprising:
a first styrene block copolymer, having an unsaturated midblock, a melt flow rate of at least about 15 g/10 minutes (190° C., 2.16 kgs) and a diblock content of no greater than about 3% by weight,
a tackifying agent, and
a plasticizer,
the hot melt adhesive composition having a viscosity of no greater than about 7,500 cps at 121° C.

20. The disposable absorbent article of claim 19 wherein the hot melt adhesive composition is used in the disposable article for an application selected from the group consisting of construction, back sheet lamination and positioning.

* * * * *